United States Patent
Borras Hidalgo et al.

(10) Patent No.: US 9,055,744 B2
(45) Date of Patent: Jun. 16, 2015

(54) NUCLEIC AND AMINO ACID SEQUENCES FOR THE CONTROL OF PATHOGEN AGENTS

(71) Applicant: Centro de Ingenieria Genetica y Biotecnologia, Ciudad de la Habana (CU)

(72) Inventors: Orlando Borras Hidalgo, Ciudad de la Habana (CU); Roxana Caridad Portieles Alvarez, Ciudad de la Habana (CU); Merardo Pujol Ferrer, Ciudad de la Habana (CU); Gil Alberto Enriquez Obregon, Ciudad de la Habana (CU); Ernesto Manuel Gonzalez Ramos, Ciudad de la Habana (CU); Camilo Ayra Pardo, Ciudad de la Habana (CU); Carlos Guillermo Borroto Nordelo, Ciudad Habana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 0 days.

(21) Appl. No.: 13/865,437

(22) Filed: Apr. 18, 2013

(65) Prior Publication Data

US 2013/0217618 A1    Aug. 22, 2013

Related U.S. Application Data

(62) Division of application No. 12/934,685, filed as application No. PCT/CU2009/000003 on Mar. 27, 2009, now Pat. No. 8,450,559.

(30) Foreign Application Priority Data

Mar. 28, 2008 (CU) .......................................... 45/08

(51) Int. Cl.
C12N 15/82 (2006.01)
A01N 37/18 (2006.01)
C07K 14/415 (2006.01)

(52) U.S. Cl.
CPC .............. *A01N 37/18* (2013.01); *C07K 14/415* (2013.01); *C12N 15/8279* (2013.01); *C12N 15/8282* (2013.01)

(58) Field of Classification Search
CPC .................................................... C07K 14/001
USPC ...................................................... 530/324
See application file for complete search history.

(56) References Cited

FOREIGN PATENT DOCUMENTS

WO 9737024 10/1997
WO 2006085965 8/2006
WO 2008080014 7/2008

OTHER PUBLICATIONS

Broekaert et al., "Plant Defensins: Novel Antimicrobial Peptides as Components of the Host Defense System", Plant Physiol, vol. 108, pp. 1353-1358; 1995.
Colilla et al., "γ-Purothionins: Amino Acid Sequence of Two Polypeptides of a New Family of Thionins from Wheat Endosperm", FEBS, vol. 270, No. 1,2, pp. 191-194; 1990.
Fant et al., "The Three-Dimensional Solution Structure of *Aesculus hippocastanum* Antimicrobial Protein 1 Determined by 1H Nuclear Magnetic Resonance", Proteins, vol. 37, pp. 388-403; 1999.
Gao et al., "Fungal Pathogen Protection in Potato by Expression of a Plant Defensin Peptide", Nature Biotechnology, vol. 18, pp. 1307-1310; 2000.
Hofgen et al., "Storage of Competent Cells for Agrobacterium Transformation", Nucleic Acids Research, vol. 16, No. 20, p. 9877; 1988.
Kawata et al., "Genetic Engineering for Disease Resistance in Rice (*Oryza sativa* L.) Using Antimicrobial Peptides", JARQ, vol. 37, pp. 71-76; 2003.
Lay et al., "Defensis-Components of the Innate Immune System in Plants", Current Protein and Peptide Science, vol. 6, pp. 85-101; 2005.
Odintsova et al., "Seed Defensins from *T. kiharae* and Related Species: Genome Localization of Defensin-Encoding Genes", Biochimie, vol. 89, pp. 605-612; 2007.
Terras et al., "Analysis of Two Novel Classes of Plant Antifungal Proteins from Radish (*Raphanus sativus* L.) Seeds", The Journal of Biological Chemistry, vol. 267, No. 22, pp. 15301-15309; 1992.
Terras et al., "Small Cysteine-Rich Antifungal Proteins from Radish: Their Role in Host Defense", The Plant Cell, vol. 7, pp. 573-588; 1995.
Thomma et al., "Plant Defensins", Planta, vol. 216, pp. 193-202; 2002.
Thomma et al., "Mode of Action of Plant Defensins Suggests Therapeutic Potential", Current Drug Targets, vol. 3, pp. 1-8; 2003.
Tschopp et al., "High-Level Secretion of Glycosylated Invertase in the Methylotrophic Yeast, *Pichia pastoris*", Bio/Technology, vol. 5, pp. 1305-1308; 1987.
Walsh et al., "New Targets and Delivery Systems for Antifungal Therapy", Medical Mycology, vol. 38, pp. 335-347; 2000.
Zambryski et al., "Ti Plasmid Vector for the Introduction of DNA into Plant Cells Without Alteration of Their Normal Regeneration Capacity", The EMBO Journal, vol. 2, No. 12, pp. 2143-2150; 1983.

*Primary Examiner* — Medina A Ibrahim
(74) *Attorney, Agent, or Firm* — Hoffmann & Baron, LLP

(57) ABSTRACT

The present invention reveals a nucleic acid sequence from *Nicotiana megalosiphon* encoding for an anti-pathogenic protein. The invention comprises the use of this nucleic acid molecule in transgenic plants of agricultural interest to confer resistance to pathogens. The invention also includes a bioproduct that comprises this anti-pathogenic protein to control plant pathogen agents.

6 Claims, 5 Drawing Sheets

(A)

(B)

(A)

(B)

(C)

(D)

(A)

(B)

(A)

(B)

NUCLEIC AND AMINO ACID SEQUENCES FOR THE CONTROL OF PATHOGEN AGENTS

CROSS-REFERENCE TO RELATED APPLICATIONS

This application is a divisional of U.S. application Ser. No. 12/934,685 filed on Sep. 27, 2010, now U.S. Pat. No. 8,450,559, which is a National Phase application of International Application No. PCT/CU2009/000003 filed Mar. 3, 2009, which claims priority based on Cuban Application No. 2008-0045 filed Mar. 28, 2008, which are incorporated herein by reference.

FIELD OF THE INVENTION

The present invention is related with the field of the agricultural biotechnology, specifically with the use of an anti-pathogenic protein in the control of pathogen agents. When the anti-pathogenic protein is applied, either by its expression in genetically modified plants, or as a bioproduct, high control levels of the diseases produced by pathogen agents of plants are obtained.

DESCRIPTION OF RELATED ART

The plant anti-pathogenic proteins have been isolated from leaves, sheaths, roots, tubers, shafts, fruits and flowers, from crop as radish, onion, medic, pepper, potato and soja. The anti-pathogenic proteins have been studied at biochemical and structural level, they are small peptides, of approximately 5 KDa, with 45 to 54 amino acids, rich in cysteines, highly basic, and charged positively. The family of the anti-pathogenic proteins of plants is diverse with regard to the amino acids composition, since only the eight cysteines that stabilize the structure seem to be conserved. This characteristic shows the diverse biological activities exhibited by the different plant anti-pathogenic proteins (Broekaert et al. (1995) Plant Physiol. 108:1353-8). The plant anti-pathogenic proteins can be divided in two groups, according to the structure of the protein precursor; in the first group the protein precursor is composed by a signal peptide from endoplasmic reticulum and a mature protein domain. This protein enters into the secretor ways and has not signals for the post-transcriptional process. In the second group, the anti-pathogenic protein is formed by a long precursor that contains besides the signal peptide and the mature domain, a C-terminal pre-domain of 33 amino acids approximately. So far, these anti-pathogenic proteins have been found only in Solanaceae species (Lay y Anderson (2005) Curr Protein Pept Sci. 6:85-101). Not all the plant anti-pathogenic proteins have the same action, some exhibit a potent activity in vitro against a wide spectrum of filamentous fungus in micromolar concentrations; others do not inhibit the fungus growth, but inhibit the α-amylase and proteins of synthesis (Colilla et al (1990) FEBS Lett. 270: 191-194).

The model Shai-Matsuzaki-Huang explains the activity of most of the anti-pathogenic proteins, which explains the interaction of the peptide with the plasmatic membrane followed by a lipidic displacement causes the formation of multimeric pores inside the plasmatic membrane due to the insertion of the positively charged protein in the cellular membrane after the occurrence of its interaction with the negatively charged fosfolipidic of the target cell surface, these multimeric pores constitute voltage-depend ion-permeable channels (Thomma et al. (2002) Planta 216:193-202).

Another model is based on the theory that many anti-pathogenic proteins produce their action not only by means of the permeabilization of the citoplasmatic membrane but also by means of citoplasmatic targets, these proteins once inside the target cell affect the deoxyribonucleic acid synthesis (DNA), ribonucleic acid (RNA) and proteins. This suggests that the ability of the cationic proteins to cause permeabilization of the citoplasmatic membrane could not be the main cause in the action mechanism, but a way of search of an intracellular target (Thomma et al. (2003) Curr Drug Targets Infect Disord. 3:1-8).

So far, many types of anti-pathogenic proteins have been identified and is characterized whose possible applications are diverse, because the genetic engineering provides a resistance strategy to plant diseases through cellular and molecular tools (Thomma et al. (2003) Curr Drug Targets Infect Disord. 3:1-8). It has been demonstrated that the constitutive expression of radish anti-pathogenic proteins increases the tobacco resistance to the pathogen of leaves *Alternaria longipes*, (Terra et al. (1995) Plant Cell 7: 573-588), of the same manner occurs in tomato plant with *Alternaria solani*. Also, the constitutive expression of an anti-pathogenic protein provides a high resistance to the fungus *Verticillium dahliae* of agronomic importance in the potato crop under field conditions (Gao et al. (2000) Nat. Biotechnol. 18: 1307-1310).

On the other hand, rice plants expressing the genes of anti-pathogenic proteins of the species *Brassica oleracea* and *B. campestris* were modified to substitute amino acids in different positions, and introduced individually into rice plants looking resistance to *Magnapothe grisea* and *Xanthomonas oryzae*; diseases of great importance in subtropical and tropical countries. These anti-pathogenic proteins conferred an effective resistance to both disease and the modification of these genes increased the wide spectrum resistance in transgenic rice (Kawata et al. (2003) JARQ 37: 71-76).

The application of the plant anti-pathogenic proteins as alternative to reduce crop losses due to the attack of pathogen constitutes an advantage with regard to the application of chemical fungicides. First: plant anti-pathogenic proteins are derived from seeds, roots and tubers, for what they constitute nature substances that are not toxic to the host plant and neither to people that consume the products from these plants. Second: as other protein, the anti-pathogenic proteins quickly degrade like native substances not leaving any residual after their effectiveness expires (Thomma et al. (2003) Curr Drug Targets Infect Disord. 3:1-8).

The plant anti-pathogenic proteins could also be used for the development of anti-fungal medications, because the control of eukaryotic pathogens has always constituted one of the main problems in the medicine, increasing in the last decades to for the increment of immunodepressed patients due to illnesses such as AIDS, cancer and organs transplant, besides the emergence of multi-drug resistant strains and the appearance of new species of filamentous fungus as yeasts that are recognized as opportunist pathogens (Thomma et al. (2003) Curr Drug Targets Infect Disord. 3:1-8).

Due to the similarity between the cells of the mammals and that of the pathogen ones, the anti-fungal compounds should act on molecules that are not or are rarely present in mammal cells, like components of the cell wall and virulence factors, and they should also be products as much natural as possible, with a wide action spectrum, easy to produce and not inducing resistance (Walsh et al. (2000) Medical Mycology, 38: 335-347). On the other hand, the fungal cell membranes are attractive targets for the development of these agents, because the components of the fungal membrane like the sphingolipids are structurally different in mammal cells. The plant antipathogenic proteins don't have as target the biosynthesis of the sphingolipids, but rather they act totally to the inverse one because their target are their own sphingolipids causing the permeabilización of the fungal membrane. This provides a high selectivity and therefore, interesting perspectives for the treatment of fungal infections. Some plant anti-pathogenic proteins have been found as: Dm-AMP1, Hs-AFP1 and Rs-AFP2 that are active in micromolar concentrations against *Cándida albicans*, a pathogen of great clinical interest in humans, which constitutes an example of the potential of this type of plant proteins for the development of the therapy (Thomma et al. (2003) Curr Drug Targets Infect Disord. 3:1-8).

An important problem to be solved is to achieve anti-pathogenic products of protein origin able to efficiently control a wide range of fungal and bacterial pathogens, aspect of a great importance in the agriculture and the medicine.

DETAILED DESCRIPTION OF THE INVENTION

This invention contributes to solve the problem mentioned above, providing the nucleotide sequence (SEQ ID No. 1) and amino acid sequence (SEQ ID No. 6) of a new anti-pathogenic protein isolated from *Nicotiana megalosiphon*. The nucleotide sequence of the invention encodes for a small cysteine rich protein, which has a marked effect over several pathogenic agents.

It is also object of the present invention, a nucleic acid that encodes for a polypeptide comprising: a) the identified amino acids sequence as SEQ ID No. 6, or b) an amino acids sequence where one or several amino acid residues have been eliminated, substituted and added to the identified sequence of amino acids as SEQ ID No. 6, which maintains its properties of controlling the infection by pathogen agents.

In an embodiment of the invention, the gene that encodes for the anti-pathogenic protein of the present invention is used to improve the resistance levels and defense is of plants toward several pathogen agents. Therefore, the present invention includes a method to increase the resistance to plant diseases caused by pathogenic agents, by means of the genetic transformation of the plant with a nucleic acid sequence: SEQ ID No. 1 that leads to the constitutive or induced expression of the anti-pathogenic protein: SEQ ID No. 6.

The molecule of nucleic acid object of the present invention can be used for the transformation of plants. In a favorite realization, the sequence of DNA that encodes for the anti-pathogenic protein can be used for the transformation of the following species of plants: *Zea mays, Brassica* sp., *Medicago sativa, Oryza sativa,* bicolor *Sorghum, Sorghum vulgare, Pennisetum glaucum, Helianthus annuus, Triticum aestivum, Glycine max, Nicotiana tabacum, Solanum tuberosum,* Ipomoea sweet potatoes, *Manihot esculenta, Coffea* spp., *Coconuts nucifera, Pineapples comosus, Citrus* spp., *Theobroma cocoa, Camellia sinensis, Muse* spp., American *Persea, Ficus casica, Psidium guajava, Mangifera indicates, Carica papaya, Beta vulgaris, Saccharum* spp., *Lycopersicon esculentum, Lactuca sativa, Phaseolus vulgaris, Cucumis sativus, Cucumis melo, Hibiscus rosasanensis, Rosa* spp., *Tulipa* spp., *Pinus taeda, Pinus elliotii,* ponderous *Pinus, Pinus contorta, Pinus radiata.*

The present invention can be used in a variety of methods in order to obtain plants of agricultural interest that produce the anti-pathogenic protein. This way, the nucleic acid sequence (SEQ ID No. 1) that encodes for the anti-pathogenic protein can be used in combination with a promoter that is introduced in a plant of agricultural interest. A constitutive promoter can be used in order to expression of high levels from anti-pathogenic protein. In other forms, the sequence that encodes for the anti-pathogenic protein can be manipulated and fused to a specific promoter to direct the expression into particular tissue in susceptible plant to a pathogen. Another object of the invention is a polypeptide with the amino acids sequence: SEQ ID No. 6 or SEQ ID No. 7. Anyone of these polypeptides has biological activity on pathogen agents, for what in this invention are denominated anti-pathogenic proteins. Another object of the invention is an amino acids sequence from a polypeptide with at least 60% of homology with the SEQ. ID No.6.

In a preferred embodiment the polypeptides or anti-pathogenic proteins of the invention are obtained for recombinant way or for chemical synthesis. The anti-pathogenic proteins of the invention can be expressed by DNA recombinant technology in different host systems, and isolated from them. In a materialization of is the invention the anti-pathogenic protein can be expressed in yeasts. In a favourite realization, the expression for DNA recombinant way is carried out in *Pichia pastoris*, preferably in the supernatant from culture. Starting from the hosts, the polypeptides of the invention can be obtained applying the techniques of isolation of proteins. The purification process can be achieved using technical immune enzymatic, chromatographic, the cellular precipitate, and other process known actually.

Variants of amino acid sequences (SEQ ID No. 6) fused with stabilizers peptides or that they direct the expression to certain compartments of the host, and maintain the biological activity demonstrated for that molecule, also they are object of the present invention. An example is fused protein whose sequence appears as SEQ ID No. 7. Fragments of the anti-pathogenic protein identified in the Listing of Sequences like SEQ ID No. 8 and SEQ ID No. 9 that retain the control activity on pathogen agents, also they are object of the present invention. Another aspect of the present invention is a bio-product for the control of pathogen agents identified as SEQ ID No. 6, SEQ ID No. 7 or a polypeptide with at least 60% of homology with the SEQ. ID No. 6.

In this invention these anti-pathogenic proteins are used, for the first time, in bio-product that confer high protection levels on the main plant diseases that taken place by pathogen agents, with high stability and low contamination, for what their use presents better public perception and less regulatory requirements. The bio-product that contains the anti-pathogenic protein of the present invention produces high protection levels on fungus and bacteria, not reported previously. To achieve the bio-product, the anti-pathogenic protein can formulate through a suspension, solution, emulsion, powder, granule, emulsifiable concentrate, aerosol, impregnated, adjuvant granule, pastures or through capsulations. In a realization of the invention, the bio-product contains the purified polypeptide from a host transformed genetically, or it is used directly contained in the super of a culture of this host. In a favorite realization the host is *P. pastoris*.

In a materialization of the invention, the anti-pathogenic proteins whose sequences are claimed can be used, as well as the bio-products that contain them, for the first time, for the control of a wide variety of pathogen as: *Aspergillus, Penicilium, Alternaria (Alternaria brassicola; Alternaria solani; Alternaria alternata); Bipolaris sacchari; Botrytis cinerea; Cercospora (Cercospora kikuchii; Cercospora zaea-maydis; Cercospora medicaginis; Cercospora sojina; Cercospora sorghi); Cladosporium fulvun; Colletotrichum (Colletotrichum lindemuthianum; Colletotrichum dematium; Colletotrichum graminicola), Diplodia maydis; Erysiphe (Erysiphe graminis* f. sp. *graminis; Erysiphe graminis* f. sp. *hordes);*

Fusarium (Fusarium nivale; Fusarium oxysporum; Fusarium graminearum; Fusarium culmorum; Fusarium solani; Fusarium moniliforme; Fusarium roseum); Helminthosporium (Helminthosporium turcicum; Helminthosporium carbonum; Helminthosporium maydis); Maganaporthe grisea; Mycosphaerella figensis; Peronospora (Peronospora manshurica; Peronospora tabacina); Phoma betae; Phytophthora (Phytophthora cinnamomi; Phytophthora cactorum; Phytophthora phaseoli; Phytophthora parasitica; Phytophthora citrophthora, Phytophthora megasperma f. sp. sojae; Phytophthora infestans), Puccinia (Puccinia sorghi; Puccinia striiformis; Puccinia graminis f. sp. tritici; Puccinia asparagi; Puccinia recondita; Puccinia arachidis; Puccinia melanocephala), Pythium (Pythium aphanidermatum; Pythium ultimum); Pyricularia oryzae; Rhizoctonia (Rhizoctonia solani; Rhizoctonia cerealis); Scerotium rolfsii; Sclerotinia sclerotiorum; Septoria (Septoria lycopersici; Septoria glycines; Septoria nodorum; Septoria tritici); Thielaviopsis basicola; Ustilago (Ustilago maydis; Ustilago scitaminea); Verticillium (Verticillium dahliae; Verticillium alboatrum); Pseudomonas syringae p.v. glycinea; Xanthomonas campestris p.v. phaseoli; Xanthomonas campestris p.v. alfalfae; Xanthomonas campestris p.v. translucens; Pseudomonas syringae p.v. syringae; Erwinia carotovorum p.v. carotovora; Erwinia stewartii; Clavibacter michiganense subsp. Nebraskense; Pseudomonas avenae; Erwinia chrysanthemi p.v. zea; Erwinia carotovora; Xanthomonas campestris p.v. holcicola, Pseudomonas andropogonis y Pseudomonas avenae. In a favorite realization the bioproducto is useful for the control of plant fungi. In a materialization of the invention the polypeptide included into the bio-product in the concentration range among 1 to 9 µg/ml.

It is also part of the present invention a method for the control of pathogen agents of plants that is characterized by the application of the bio-product to the plants which comprises an identified polypeptide with SEQ ID No. 6, SEQ ID No. 7 or a polypeptide with at least 60% homology with the SEQ. ID No. 6. In another materialization of the invention, the method for the control of pathogen agents of plants is characterized by the application of the bio-product of the invention in combination with bio-pesticides. Genetically modified plants with the sequence of nucleic acid: SEQ ID No. 1, or a nucleic acid sequence from SEQ ID No. 1 (transgenic plants), to increase the resistance to plant diseases produced by is pathogen agents, are also part of the present invention.

BRIEF DESCRIPTION OF THE DRAWINGS

(FIG. 3A) Effect of *Peronospora hyoscyami* f. sp *tabacina* on tobacco leaves. (FIG. 3B) Effect of *Alternate solani* on potato leaves. (FIG. 3C) Effect of *Phytophthora parasitica* on tobacco stems. (FIG. 3D) Effect of *Phytophthora infestans* on potato leaves. In the figures the bars represent: a. inoculated control, b. not inoculated control, c. clone 1.1, d. clone 1.2, e. clone 1.3.

EXAMPLES

Example 1

Preparation of the vegetable material, isolation and cloning of the DNA that encodes for the antipathogenic protein NmDef-02 from *Nicotiana megalosiphon*

The *N. megalosiphon* specie was grow in pots of 6 inches that contained black crowd and shell of rice in a proportion (4:1) and maintained in green house condition at 23° C. An isolate of *Peronospora hyoscyami* f. sp. *tabacina* collected of a tobacco field in Havana was used in the inoculations. The inoculations were carried out in plants of this specie with 6 weeks of age, placing several drops of 10 µl with a concentration of $5\times10^3$ spores per ml. The plants were placed in black plastic bags with high humidity (the humidity was achieved atomizing water inside the bags) during a period of 12 hours, to promote the infection.

The total RNA was extracted of leaves from *N. megalosiphon* inoculated 6 days later, using the system of extraction of total RNA for spin (Promega, Madison, Wis., USA). Finally, the cDNA double chain was synthesized (cDNA), using the system of synthesis of cDNA from Promega.

The cDNA library was made using subtractive hybridization using the system of suppression subtractive hybridization selective (Clontech, Palo Alto, AC, USA). The cDNA obtained from *N. megalosiphon* plants inoculated with *P. hyoscyami* and harvested 6 days after the inoculation, was used as sample for the subtraction. The subtractive library was cloned in the pGEM-T Easy vector (Promega) according to the instructions.

The sequencing of the cDNA was developed using an automatic sequencer. After the analysis of the sequences, a DNA sequence was selected that had low homology levels with proteins reported in databases, which was used in the later experiments.

Example 2

Plant Transformation with the Gene of the Antipathogenic Protein NmDef-02

Production of Tobacco Transgenic Plants: Construction of the Binary Vectors.

Figure 1:
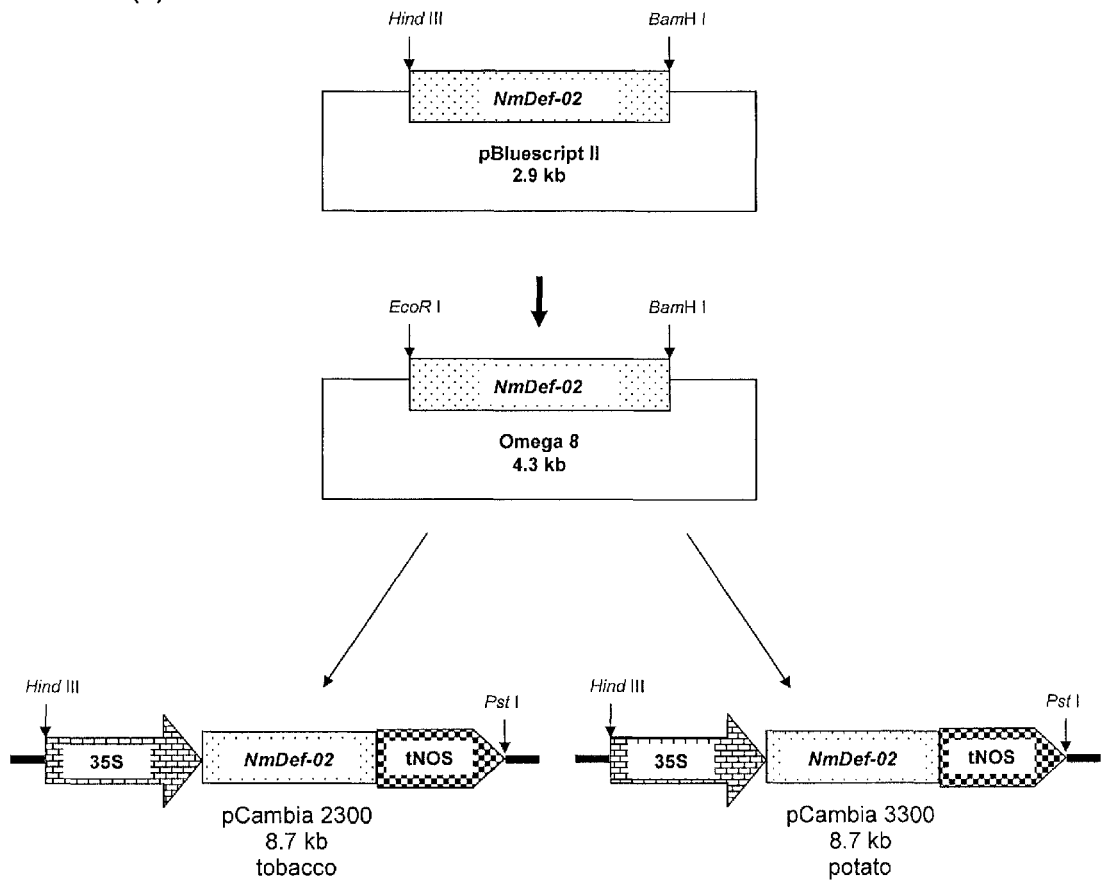
FIG. 1. Cloning strategy of interest antipathogenic protein in the expression vectors in plants (FIG. 1A) and yeast (FIG. 1B).
Figure 1:
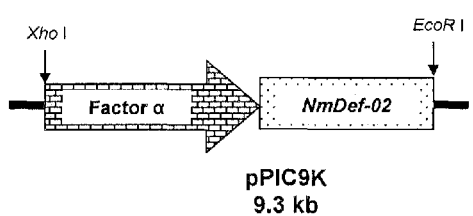

In this experiment the complete cDNA of the gene that encodes for the antipathogenic protein was isolated with the oligo nucleotides SEQ ID No. 2 and SEQ ID No. 3 and cloned in the transformation vector "pCambia 2300" in the restriction sites Hind III/Pst I (FIG. 1A). The genetic transformation of plants of *Nicotiana tabacum* was carried out by the method from Zambryski et al. (1983) EMBO Journal, 2: 2143-2150. For this proposal, the strain AT 2260 of *Agrobacterium tumefaciens* was using the method of the liquid nitrogen (Hofgen and Willmitzer (1988) Nucl. Acids Res. 16: 9877) with the developed binary vector. Leaves disks of *N. tabacum* plants of the variety Petit Havana SR 1 cultivated in vitro were transformed. Kanamycin was used to 100 mg/L as marker agent. The disks leaves were co-cultivated with the recombinant *Agrobacterium* for 48 hours in Murashige and Skoog (MS) liquid medium. The tobacco plant regeneration (4-6 weeks) was made on MS medium that contained: sucrose 25 g/L, 6-Bencil amino purine (BAP) 1 mg/L, acetic naftalen acid (ANA) 0.1 mg/L, kanamycin 100 mg/L and claforan (Claf) 500 mg/L. The plant rooting (1-3 weeks) carried out on MS that contained: sucrose 30 g/L, kanamycin 100 mg/L and Claf 500 mg/L.

Production of Potato Transgenic Plants: Construction of the Binary Vectors

In this experiment the complete cDNA of the gene that encodes for the antipathogenic protein was isolated with the oligo nucleotides of the SEQ ID No. 2 and SEQ ID No. 3 and cloned in the transformation vector "pCambia 3300" in the restriction sites Hind III/Pst I (FIG. 1A). The vegetable material that was used in the experiments of tissue culture and transformation was taken of in vitro plants from the cultivar of potato "Desiree." The plants were grown in test tubes on MS medium. The pH of the culture medium was adjusted at 5.7. Plants of four weeks of cultivation were used, maintained in rooms with 25° C. and an illumination of 2000 Lux. The culture medium that served as base for the regeneration experiments and transformation were the SC (MS salts, vitamin B1 0.4 mg/L, myo-inositole 100 mg/L, sucrose 20 g/L, BAP 3.5 mg/L, ANA 0.01 mg/L, phytoagar 6 g/L), the SB (MS salts, myo-inositole 100 mg/L, sucrose 20 g/L, $AG_3$ 3.5 mg/L, phytoagar 6 g/L) and the PP (MS salts, vitamin B1 0.4 mg/L, myo-inositole 100 mg/L, pantothenate of calcium 2 mg/L, sucrose 30 g/L, phytoagar 6 g/L, activated carbon 5 g/L and Nitrate of Silver-thiosulfate of Sodium 1 mg/L (STS).

For the transformation the strains of *Agrobacterium* "At2260" and "LBA 4404" were used. The bacteria was cultivated in a culture medium with yeast extract 1 g/L, bactopeptone 1 g/L, sucrose 5 g/L and Lab-lemco powdered 5 g/L, to 28° C. in the dark condition until reached an optical density $(DO)_{620}$ 0.7-0.9.

The procedure of transformation-regeneration was developed in two stages, in the is following way: segments of stems of in vitro plants of 4 weeks of cultivation were incubated on MS medium during 12-16 hours at 25° C. in dark, then the infection with *A. tumefaciens* was developed by means of the incubation of the explantes during 7 minutes with 1 mL of the bacterial suspension for each 20 ml of MS medium; the explantes were co-cultivated on SC medium during 48 hours at 22° C. in dark and the explantes was placed on a sterile filter paper. The washing of the explantes on MS medium and drying with sterile filter paper was carried out carefully. In a first stage they were cultivated during 15 days on light condition on selective medium SC, 500 mg/L of claforan and 5 mg/L Phosphinothricin (PPT) and in a second stage they were cultivated on light condition on selective medium SB, 500 mg/L of claforan and 5 mg/L PPT. Finally the small plants were individualized on selective medium PP, with 500 mg/L of claforan and selected in 5 mg/L of PPT.

Example 3

Evaluation of the Effect of the Antipathogenic Protein NmDef-02 on the Disease Resistance Experiment of Tobacco Disease Resistance to *Peronospora hyoscyami* f. sp. *Tabacina*.

Figure 3:
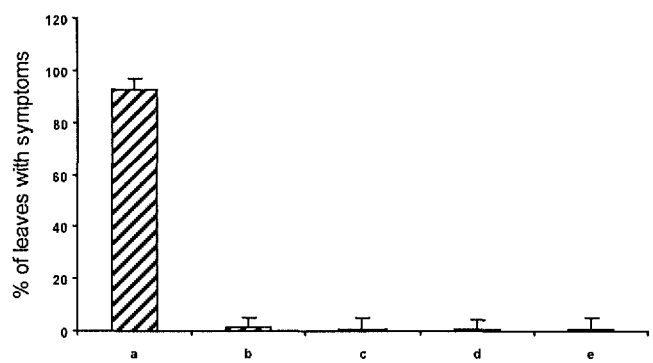
FIG. 3. Experiment of constitutive expression of the antipathogenic protein in transgenic plants and evaluation of the disease resistance. The figure represents the percentage of leaves and stems with disease symptoms in the controls samples and the transgenic clones expressing the antipathogenic protein.
Figure 3:
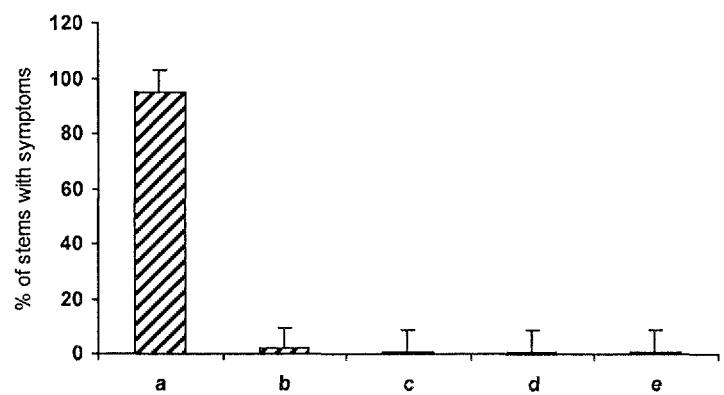
Figure 3:
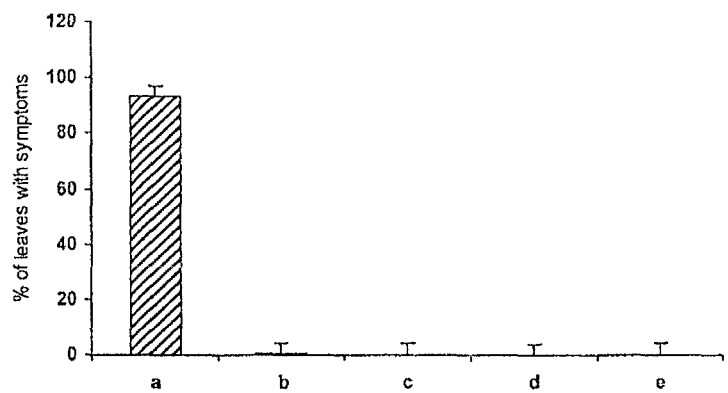
Figure 3:
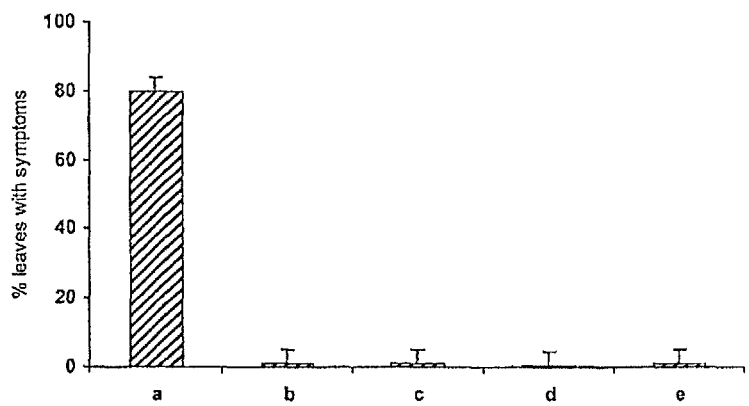

Plants with roots, resistance to the kanamycin antibiotic and with the gene of the antipathogenic protein were planted in pot for its adaptation in green house condition during 45 days. After that period a group of 100 transgenic clones of 6 weeks old were inoculated with a suspension of *P. hyoscyami* f. sp. *tabacina* placing several drops of 10 µl with a concentration of $5 \times 10^3$ spores/ml. The plants were placed in black plastic bags and spraying with water during a period of 12 hours, to promote the infection. The evaluation of the susceptibility was carried out measuring the percentage of leaves with symptoms of the disease one week later (FIG. 3A). As it can be appreciated in the FIG. 3A high resistance levels were achieved to this pathogen, when we compare the percentage of leaves with symptoms between the inoculated control and the different clones, which shows the utility of the antipathogenic protein used for the control of this important pathogen.

Experiment of Tobacco Disease Resistance to *Phytophthora parasitica*.

Plants with roots, resistance to the kanamycin antibiotic and with the gene of the antipathogenic protein were planted in pot for its adaptation in green house during 45 days. After that period a group of 100 transgenic clones of 6 weeks old were inoculated with *P. parasitica* and the percentage of stem with disease symptoms was evaluated one month later.

For the evaluation procedure the pathogen *P. parasitica* was grown in Petri plate that contained Potato Dextrose Agar medium (PDA) at a concentration of 39 g/L. The pathogen was incubated at 27° C., during 10 days. For the inoculation of tobacco plants a PDA disk (diameter=1 cm) with the pathogen was placed in the base of the stem and incubated at 28° C., with high humidity FIG. 3B). As it can be appreciated in the FIG. 3B the clones expressing the antipathogenic protein achieved high resistance levels never seen before to this soil pathogen that causes important losses in the seedling phase of this crop. This result demonstrates that it is feasible the use of this protein for the control of this pathogen.

Experiment of Potato Disease Resistance to *Phytophthora infestans*

This test consisted in inoculation of *Phytophthora infestans* in potato transgenic plants of 5 weeks old under controlled conditions of light, temperature and relative humidity. About 100 clones of 5 weeks old that express the antipathogenic protein were spreading, with a suspension of $10^6$ zoospores/ml. The clones were maintained under controlled conditions with a relative humidity between 85-95% and a temperature of 23° C. The percentage of leaves with symptoms was used as measure of susceptibility to the pathogen one week after the inoculations (FIG. 3C). This was an unexpected result, since this pathogen is extremely difficult to control. In the FIG. 3C, the clones expressing the antipathogenic protein showed high resistance levels, compared with the controls. This result points out the potential for the use of this protein in the control of this pathogen in particular, for its importance at world level.

Experiment of Potato Disease Resistance to *Alternaria solani*

The fungus *Alternaria solani* was inoculated in 100 potato transgenic plants of 5 weeks old under controlled conditions of light, temperature and relative humidity. The clones were spreading with a suspension of $10^6$ spores/ml. The clones were maintained under controlled conditions with a relative humidity between 85-95% and a temperature of 20° C. The percentage of leaves with symptoms was used as measure of susceptibility to the pathogen one week after the inoculations (FIG. 3D). The three analyzed clones showed high resistance levels to this pathogen, which for the first time offers a potential for the use of this protein for the control.

Example 4

Construction of the Expression Vector of the Antipathogenic Protein NmDef-02, in an Extracellular Way, in the Super of *Pichia pastoris* Culture The gene that encodes for the antipathogenic protein from *N. megalosiphon* was isolated using the specific oligo nucleotides corresponding to the SEQ ID No. 4 and SEQ ID No. 5 to obtain the complete sequence of the gene that encodes for the antipathogenic protein NmDef-02, with the enzymatic restriction sites Xho I/EcoR I, necessary for the cloning in the expression vector pPIC9k. This cloning strategy adds to the protein of interest in the end amino-terminal the signal peptide of the factor alpha of *Saccharomyces cerevisiae* (FIG. 1B), for what the resulting protein belongs to the SEQ ID No. 7. The plasmid was linearized with Bgl II before transforming the strain GS115 of *P. pastoris*. The transformation was carried out by electroporation. The strain GS115 is a mutant auxotrophic his3 which acquires a phenotype His+ after the transformation. The clones His+ was selected on minimum glucose medium; the clones were cultivated on minimum glycerol medium and induced with methanol during 126 hours at 28° C.

The transformed clones were identified by Dot-Blot. Using the technique of Southern Blot was determined in which the integration had happened for substitution of the gene AOX1 from *P. pastoris* for the expression of recombinant plasmid, which is correspondence with a phenotype Mut$^s$ (low methanol) and His$^+$. *P. pastoris* secrets low levels of own proteins and its culture medium doesn't need proteins supplements, for can be hope that a protein that is secreted to the subcellular medium, which constitute most of the total of proteins in the culture (more than 80%) (Tschopp et al. (1987) Bio/Technology 5:1305-1308). The expression of the antipathogenic protein in *P. pastoris* was carried out in bash of 5 litres by addition of the methanol to the culture medium. The expression of the antipathogenic protein and its integrity were checked by mass spectrophotometry.

Example 5

Figure 2:
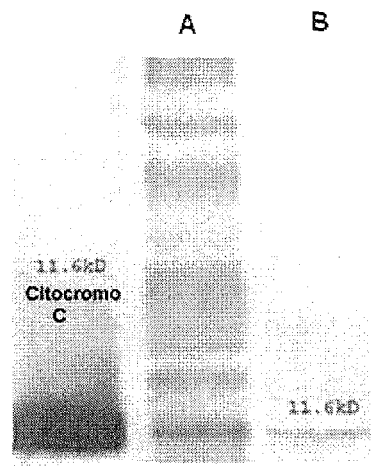
FIG. 2. Expression of the antipathogenic protein in *Pichia pastoris*, using the pPIC9K vector, fused to the signal peptide from the *Saccharomyces cerevisiae* alpha factor. Production of the antipathogenic protein in the supernatant of *P. pastoris* (A) and in the purified fraction (B).

Purification and Assay of the Biological Activity of the Antipathogenic to Protein The antipathogenic protein fused to the signal peptide of the alpha factor (NmDef-Plus) was purified from the supernatant of the culture medium, by dialysis in 25 mm of acetate of sodium to pH 4.5; the product of the dialysis spent through a resin of cationic exchange CM-Sepharosa balanced Fastflow with 25 mm of acetate of sodium, pH 4.5; and proteins were eluted with 1 M sodium chloride, 50 mm of Tris pH 7.6. The fractions that contained the protein were collected and concentrated using an ultra-spin system with a membrane with a pores size (cut-off) of 3 kDa. For the detection a wavelength of 254 nm was used. The purification was checked by electrophoresis in polyacrylamide gel with SDS-PAGE, Sodium Dodecyl Sulphate-Polyacrylamide Gel Electrophoresis (15% ris-Glicne) and the proteins were visualized by silver staining (FIG. 2).

The antifungal activity of the antipathogenic protein was quantified through the spectrophotometry method and the analysis of the mycelium by staining with blue lactophenol through optic microscopy (Terras et al. (1992) J. Biol. Chem. 267: 14301-15309). The evaluation was carried out in 96 wells-plates, in which 50 μL of potato-glucose liquid medium, 50 μL of spores suspension of the pathogen and 20 μL of the antipathogenic protein partially purified were added.

The percentage of inhibition of the growth (PIC) of the pathogen was determined according to that reported previously (Terras et al. (1992) J. Biol. Chem. 267: 14301-15309), by means of the following equation:

$$PIC = \frac{DO_{595\,nm}\ \text{control} - DO_{595\,nm}\ \text{treatment}}{DO_{595\,nm}\ \text{control}} \times 100$$

Figure 4:
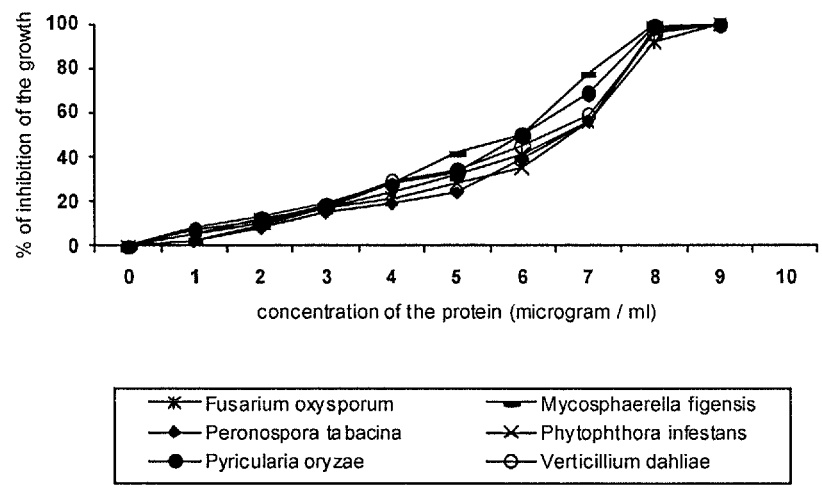
FIG. 4. Experiment of activity of the antipathogenic protein on several plant pathogens to different concentrations. The graph represents the percentage of inhibition of the growth in liquid medium from the pathogen handled to different concentrations of the antipathogenic protein fused to the signal peptide of the alpha factor (A) and synthesized without the signal peptide (B). Legend of the FIG. 4B: □ effect of the protein fused to the signal peptide of the alpha factor on *Phytophthora infestans*, ♦ effect of the protein without the signal peptide on *Phytophthora infestans*, ■ control.
Figure 4:
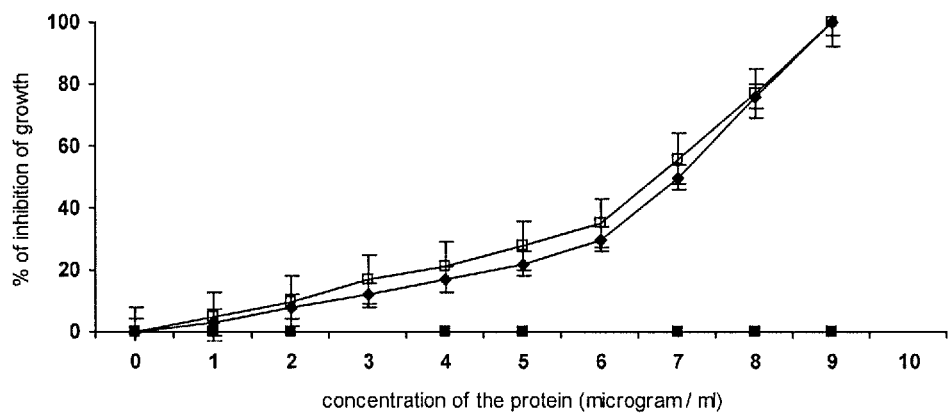

The relation among inhibition percentages comes from the application of the former equation to the realized readings (to 595 nm) of the controls and the treated samples 48 hours after the assay was initiate (FIG. 4A).

The antipathogenic protein without the signal peptide of the alpha factor was chemically synthesized, and its effect was evaluated on the pathogen *P. infestans* to different concentrations according to previous report (Terras et al. (1992) J. Biol. Chem. 267: 14301-15309) (FIG. 4B).

In FIGS. 4A and 4B, the antipathogenic protein achieved high levels of inhibition growth of plants pathogens, either fused to the signal peptide of the alpha factor or to chemically synthesized without the signal peptide. It was very interesting to observe, for the first time, the inhibition of important pathogens of plants, not achieved until the moment by other antifungal proteins reported. Another non prospective result and that allows the employment of this antipathogenic protein with a wide action spectrum, were the high inhibition levels that showed in bacterial pathogen (Table 1).

TABLE 1

Effect of the antipathogenic protein NmDef-02 on bacterial pathogens.

| Bacteria Species | IC$_{50}$ (μM) |
| --- | --- |
| *Xanthomonas campestris* p.v. *phaseoli* | 40 ± 3 |
| *Pseudomonas syringae* p.v. *syringae* | 26 ± 6 |
| *Erwinia carotovorum* p.v. *carotovora* | 86 ± 8 |
| *Pseudomonas avenae* | 17 ± 5 |
| *Erwinia chrysanthemi* p.v. *zea* | 11 ± 8 |

IC$_{50}$: concentration of NmDef-02, where the bacteria growth is inhibit in a 50%.
± Media standard deviation.

Example 6

Demonstration of the Control of a Formulation of the Antipathogenic Protein NmDef-02 on Soil and Air Fungal Pathogen Seeds of the *N. tabacum* species were treated with the formulation of the antipathogenic protein (9 μg/ml) and 5% of sodium alginate, after that they were germinated in 6 inches pots that contained black crowd and rice in a proportion (4:1) and maintained in greenhouse at 23° C. As controls treatments were used seed treated with 10% of hypochlorite of sodium and others without any treatment type. The evaluations were carried out at 30 days and the percentage of dead plants due to natural infection was determined (FIG. 5A).

On the other hand, 100 plants in greenhouse were spraying with the formulation of the antipathogenic protein with a concentration of the active principle of 5 µg/ml and 5% sodium alginate. For controls, aspersions with the fungicidal Benomil at concentration of 40 g/L and water were used. The percentage of leaves with symptoms was evaluated through of the natural infection, at 45 days after the application of treatments (FIG. 5B).

Figure 5:
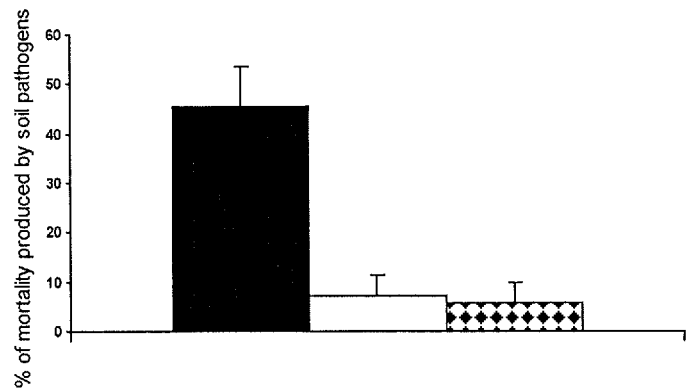
FIG. 5. Experiment of the control effect on soil (A) and air (B) pathogens of the formulation of the antipathogenic protein NmDef-02. In the figure the bars represent: ■ control plants, □ plants treated with fungicides, ♦ plant treated with the formulation to of the antipathogenic protein.
Figure 5:
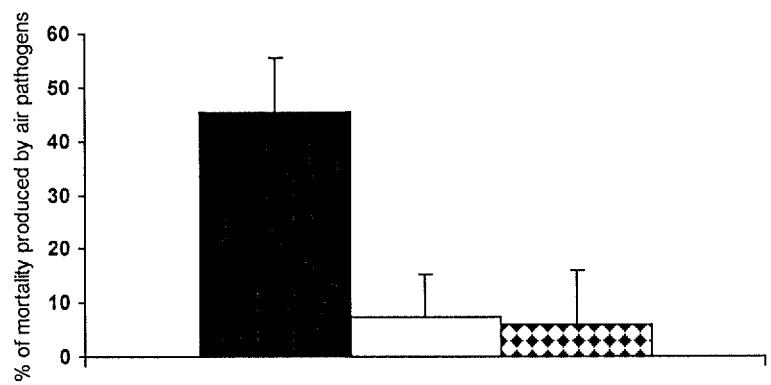

In the FIGS. 5A and 5B the formulation of the antipathogenic protein achieved the control of soil and air fungal pathogen in comparison with the controls used; this result has not been reported until the moment, allowing the use of this protein as a bioproduct in the control of plant pathogens.

Example 7

Biological Activity of Fragments of the Antipathogenic Protein NmDef-02

Figure 6:
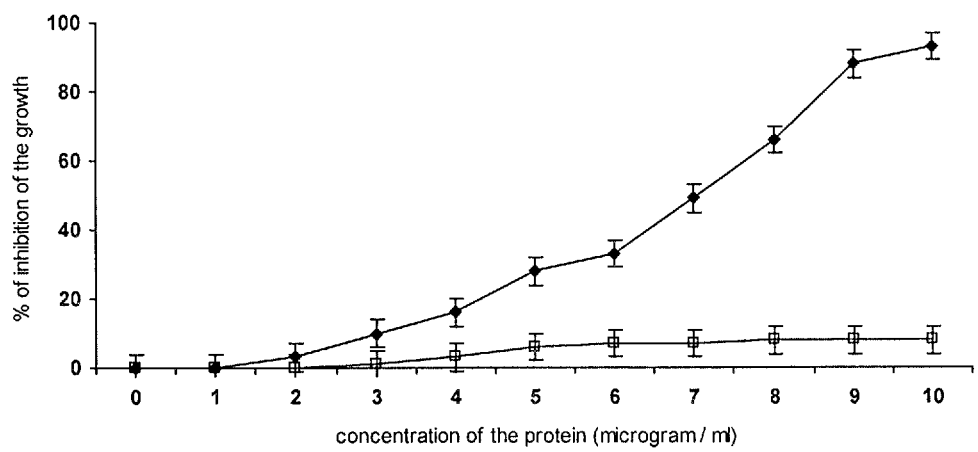
FIG. 6. Biological activity of fragments of the antipathogenic protein NmDef-02 on *Phytophthora infestans*. □ effect of the peptide SEQ ID No 8 on *Phytophthora infestans*, ♦ effect of the peptide SEQ ID No 9 on *Phytophthora infestans*.

Fragments of the antipathogenic protein NmDef-02 were obtained by chemical synthesis (SEQ ID No. 8 and SEQ ID No. 9). The effect on the pathogen *P. infestans* was evaluated to different concentrations according to the information reported (Terras et al. (1992) J. Biol. Chem. 267: 14301-15309), which is shown in FIG. 6. The obtained result allows the use of fractions of the protein to achieve the control or inhibition of pathogen when the fraction of the protein of the SEQ ID No. 9 is used.

Incorporation Of Sequence Listing

Incorporated herein by reference in its entirety is the Sequence Listing for the application. The Sequence Listing is disclosed on a computer-readable ASCII text file titled, "sequence_listing.txt", created on Apr. 17, 2013. The sequence_listing.txt file is 4 kb in size.

The invention claimed is:

1. A method for the control of pathogen agents of plants said method comprising application of a bioproduct that comprises the polypeptide identified as SEQ ID NO: 6 or SEQ ID NO: 7 to the plants.

2. The method according to claim 1, wherein the polypeptide is purified from a genetically transformed host or it is used directly as contained in a supernatant of a culture of such a host.

3. The method according to claim 2, wherein the host is *P. pastoris*.

4. The method according to claim 1, wherein the pathogen agent is a fungal pathogen.

5. The method according to claim 1, wherein the polypeptide is in a concentration range between 1 to 9 μg/ml.

6. A method for the control of pathogen agents of plants said method comprising application of a bioproduct that comprises the polypeptide identified as SEQ ID NO: 6 or SEQ ID NO: 7 mixed with biopesticides to the plants.

* * * * *

SEQUENCE LISTING

<160> NUMBER OF SEQ ID NOS: 9

<210> SEQ ID NO 1
<211> LENGTH: 141
<212> TYPE: DNA
<213> ORGANISM: Nicotiana megalosiphon

<400> SEQUENCE: 1

```
atgcgtgagt gcaaggctca gggccgtcac actacgtgtt tcgtgacgc gaactgcgtc        60 caagtctgtg aaaaacaggc tggctggtca cacggggact gccgagcaca gttcaagtgc       120
aaatgtatat tcgagtgcta a                                                 141
```

<210> SEQ ID NO 2
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 2

```
aagcttatgc gtgagtgcaa ggctc                                              25
```

<210> SEQ ID NO 3
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 3

```
ctgcagttag cactcgaata tac                                                23
```

<210> SEQ ID NO 4
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 4

```
ctcgagatgc gtgagtgcaa ggctc                                              25
```

<210> SEQ ID NO 5

-continued

<210> SEQ ID NO 5
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 5
gaattcttag cactcgaata tac                                           23

<210> SEQ ID NO 6
<211> LENGTH: 45
<212> TYPE: PRT
<213> ORGANISM: Nicotiana megalosiphon

<400> SEQUENCE: 6

Arg Glu Cys Lys Ala Gln Gly Arg His Thr Thr Cys Phe Arg Asp Ala
 1               5                  10                  15

Asn Cys Val Gln Val Cys Glu Lys Gln Ala Gly Trp Ser His Gly Asp
            20                  25                  30

Cys Arg Ala Gln Phe Lys Cys Lys Cys Ile Phe Glu Cys
        35                  40                  45

<210> SEQ ID NO 7
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 7

Ala Pro Val Asn Thr Thr Thr Glu Asp Glu Thr Ala Gln Ile Pro Ala
 1               5                  10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Arg Glu
    50                  55                  60

Cys Lys Ala Gln Gly Arg His Thr Thr Cys Phe Arg Asp Ala Asn Cys
65                  70                  75                  80

Val Gln Val Cys Glu Lys Gln Ala Gly Trp Ser His Gly Asp Cys Arg
                85                  90                  95

Ala Gln Phe Lys Cys Lys Cys Ile Phe Glu Cys
            100                 105

<210> SEQ ID NO 8
<211> LENGTH: 24
<212> TYPE: PRT
<213> ORGANISM: Nicotiana megalosiphon

<400> SEQUENCE: 8

Arg Glu Cys Lys Ala Gln Gly Arg His Thr Thr Cys Phe Arg Asp Ala
 1               5                  10                  15

Asn Cys Val Gln Val Cys Glu Lys
            20

<210> SEQ ID NO 9
<211> LENGTH: 21
<212> TYPE: PRT
<213> ORGANISM: Nicotiana megalosiphon

<400> SEQUENCE: 9

-continued

```
Gln Ala Gly Trp Ser His Gly Asp Cys Arg Ala Gln Phe Lys Cys Lys
  1               5                  10                  15

Cys Ile Phe Glu Cys
             20
```